United States Patent [19]

Collins et al.

[11] Patent Number: 4,595,399
[45] Date of Patent: Jun. 17, 1986

[54] NEBULIZATION REFLUX CONCENTRATOR

[75] Inventors: Vernon G. Collins, Poquoson; Wesley R. Cofer, III, Grafton, both of Va.

[73] Assignee: The United States of America as represented by the Administrator of the National Aeronautics and Space Administration, Washington, D.C.

[21] Appl. No.: 668,432

[22] Filed: Nov. 5, 1984

[51] Int. Cl.$^4$ ............................................. B01D 47/02
[52] U.S. Cl. ........................................ 55/255; 55/259; 55/521; 55/528; 261/78 A
[58] Field of Search ............... 55/68, 70, 71, 73, 97, 55/85, 90, 270, 255, 259, 521, 528; 261/78 A; 239/338; 73/863.21

[56] References Cited

U.S. PATENT DOCUMENTS

| | | |
|---|---|---|
| 1,847,368 | 3/1932 | Wendler ................................ 55/97 |
| 2,760,922 | 8/1956 | Williams ........................... 261/78 A |
| 2,943,460 | 7/1960 | Brown ................................. 55/521 |
| 3,064,409 | 11/1962 | Schmitt . |
| 3,134,825 | 5/1964 | Sexton ............................. 261/78 A |
| 3,240,002 | 3/1966 | O'Rourke et al. .................... 55/528 |
| 3,339,351 | 9/1967 | Carmichael, Jr. et al. . |
| 3,455,792 | 7/1969 | Ohta ..................................... 55/97 |
| 3,581,473 | 6/1971 | Ririe, Jr. et al. ...................... 55/270 |
| 3,625,491 | 12/1971 | Yokoi . |
| 3,920,419 | 11/1975 | Schroeder et al. .................... 55/70 |
| 3,960,523 | 6/1976 | Ryan .................................... 55/270 |
| 3,977,254 | 8/1976 | Brouwer .............................. 55/270 |
| 4,208,912 | 6/1980 | Baldeck . |
| 4,239,516 | 12/1980 | Klein . |
| 4,293,378 | 10/1981 | Klein . |
| 4,344,775 | 8/1982 | Klein . |
| 4,437,867 | 3/1984 | Lerner . |
| 4,460,552 | 7/1984 | Zakrzewski ........................... 55/68 |

Primary Examiner—Bernard Nozick
Attorney, Agent, or Firm—Howard J. Osborn; Wallace J. Nelson; John R. Manning

[57] ABSTRACT

A nebulization reflux concentrator 10 for removing trace gas contaminants from a sample gas is disclosed. Sample gas from a gas supply 40 is drawn by a suction source 42 into a vessel 11. The gas enters vessel 11 through an atomizing nozzle 16, thereby atomizing and entraining a scrubbing liquid solvent drawn through siphon tube 22 from a scrubbing liquid reservoir 21. The gas and entrained liquid rise through concentrator 10 and impinge upon a solvent-phobic filter 28, whereby purified gas exits through filter 28 and contaminated liquid coalesces on filter 28 and falls into reservoir 21.

2 Claims, 1 Drawing Figure

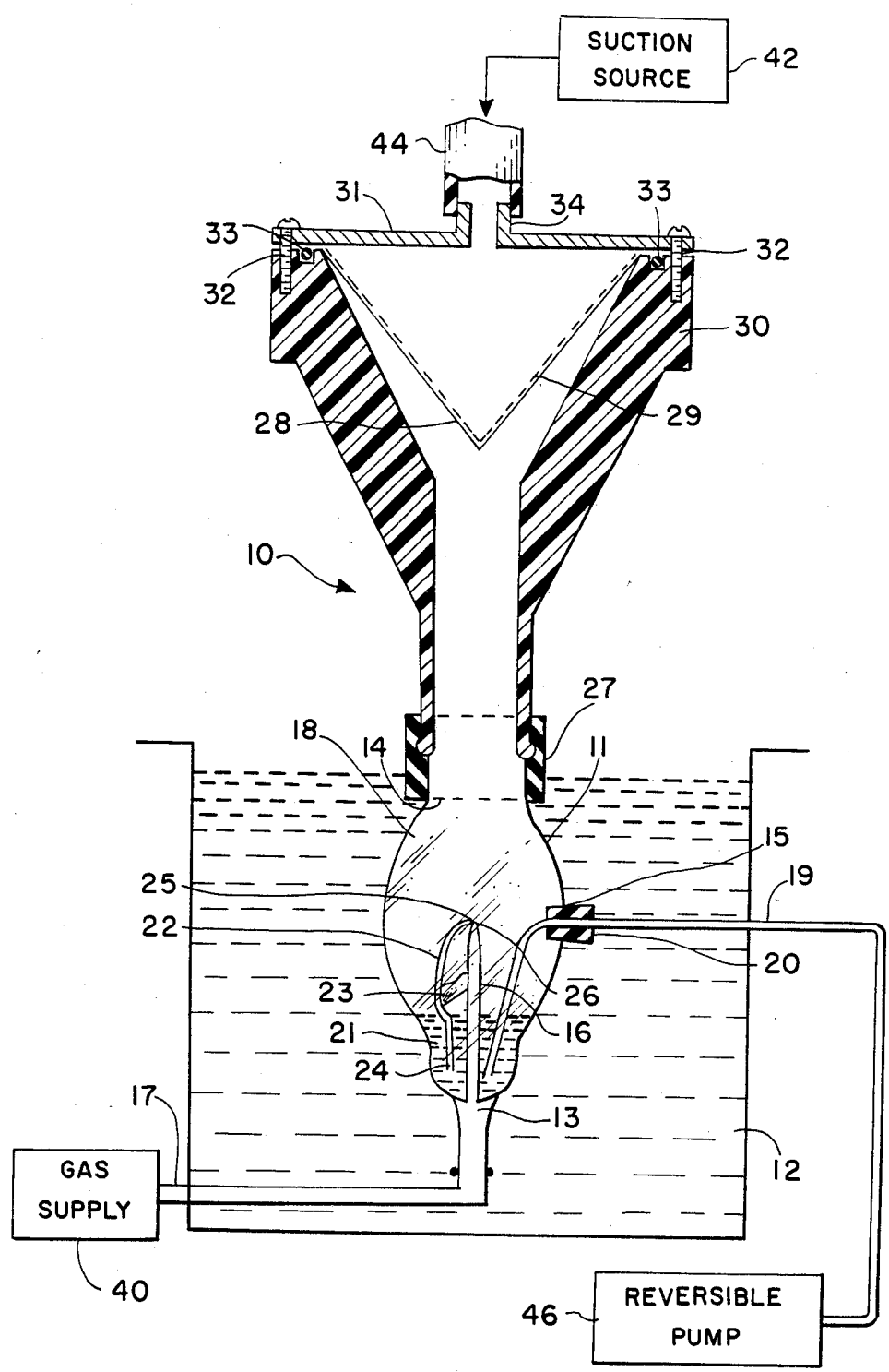

NEBULIZATION REFLUX CONCENTRATOR

ORIGIN OF THE INVENTION

The invention described herein was made jointly in the performance of work under NASA Contract No. NAS1-17303 with the College of William and Mary and an employee of the U.S. Government. In accordance with 35 USC 202, the contractor elected not to retain title.

BACKGROUND OF THE INVENTION

This invention relates to improvements in gas absorption techniques, and more particularly concerns a reflux concentrator for scrubbing contaminated gases with a solvent liquid. This invention is especially useful in measuring indirectly the trace levels of discrete constituents present in studied sample gases.

Many constituents exist in the atmosphere as trace gases. Despite the minute concentrations of these atmospheric constituents, trace gas constituents can greatly affect the quality of both the atmosphere and the environment as a whole. Such an impact on atmospheric and environmental quality compels the monitoring of these trace constituents. Since directly measuring the minute concentrations of these trace constituents is often impractical if not impossible, preconcentration to measurable levels is usually necessary when using conventional equipment. A commonly used method of preconcentration is gas absorption, whereby trace constituents from a large amount of sample gas are removed and concentrated in a fixed quantity of scrubbing liquid. The concentrated levels of trace constituents in the liquid are readily measured thus providing a basis for calculating the constituent content level of the prescrubbed sample gas. Most of the devices employed for gas absorption fall into the broad categories of bubblers or sprayers. These devices are typically too cumbersome and slow for field use as they require both large quantities of scrubbing liquid and long sampling periods to reach measurable concentration levels. If preconcentration could be achieved more quickly and with less scrubbing liquid, field measurements would be greatly facilitated.

Accordingly, it is an object of this invention to provide a gas absorption device facilitating measurements of trace gases present in sample gases.

Another object of this invention is to provide a gas absorption device permitting field operation by semiskilled operators.

Another object of this invention is to provide a gas absorption device requiring less scrubbing liquid for a given quantity of sample gas than required by conventional scrubbers achieving the same extraction efficiency.

Another object of this invention is to provide a gas absorption device requiring less time to reach a measurable concentration level of trace constituents in its scrubbing liquid for a given quantity of gas than the time required by conventional scrubbers achieving the same extraction efficiency.

Yet another object of this invention is to provide a gas absorption device capable of scrubbing higher gas flow rates (8 1/min and above) than are processable with conventional scrubbers of similar size achieving the same extraction efficiency.

A further object of the invention is to provide a gas absorption device with sufficiently low back pressure at a 8 1/min sample inlet rate to permit direct sampling from an aircraft without the need for pumps.

SUMMARY OF THE INVENTION

According to the present invention, the foregoing and additional objects of the present invention are achieved by utilizing a nebulization reflux concentrator having a nebulizing vessel with a solvent-phobic filter mounted over an enlarged outlet gas exit opening. The nebulizing vessel has an inlet nozzle in its base through which a prescrubbed sample gas is blown. An open-ended tube inside the vessel is positioned with one open end in the path of the nozzle exit and with the the other open end adjacent to the base of the vessel. The bottom of the vessel is filled with scrubbing liquid, submerging the lower end of the tube. The rush of gas out of the nozzle tip past the upper end of the tube creates suction which draws scrubbing liquid up through the tube and out into the rising gas stream. As the scrubbing liquid enters the rising gas stream, the liquid is atomized, and a two-phase mist fills the vessel. Intimate contact occurs between the two phases, as trace constituents leave the sample gas and enter the scrubbing liquid. The mist is drawn to the gas exit opening by external suction. The hydrophobic filter covering the exit opening traps the entrained liquid inside the vessel while allowing the scrubbed gas to exit virtually unimpeded. The trapped liquid coalesces on the filter surface and drops back into the scrubbing liquid pool in the bottom of the vessel. The entrained scrubbing liquid is repeatedly aspirated, atomized, filtered, and returned to the scrubbing liquid pool; this reflux is the essential preconcentration step. Make-up scrubbing liquid is added as necessary through a fill/drain tube extending through a side opening in the vessel. After the scrubbing liquid contains trace gas constituents of a measurable level, the system is shut down. The entrained scrubbing liquid is then withdrawn and the vessel is rinsed with fresh scrubbing liquid to remove all trace constituents. The rinse is added to the withdrawn scrubbing liquid, and the trace constituents concentration level of the combined scrubbing liquid is measured. With the total amount of gas scrubbed being known, the contaminant concentration of the inlet prescrubbed gas is easily calculated.

BRIEF DESCRIPTION OF THE DRAWINGS AND TABLES

A more complete appreciation of the invention and many of the attendant advantages thereof will be readily apparent as the same becomes better understood by reference to the following description when considered in connection with the accompanying drawing wherein:

The single Figure is a side view, part schematic, cross-section of the nebulization reflux concentrator of the present invention.

DETAILED DESCRIPTION OF THE INVENTION

Referring now to the drawing, there is shown the nebulization reflux concentrator according to the present invention and generally designated by the numeral 10. The base of the concentrator 10 is a vessel 11 immersed in an isothermal bath 12. Vessel 11 is provided with an inlet 13, an outlet 14, and a side opening 15. Inlet 13 receives atomizing nozzle 16 through which a prescrubbed sample gas stream is drawn from inlet tube 17. A suitable gas supply as schematically shown and designated by reference numeral 40 serves to supply the test gas to tubular inlet 17 as will be further explained hereinafter. Outlet 14 provides for communication between the scrubbing chamber 18 and a solvent-phobic membrane/filter 28. Side opening 15 receives fill/drain tube 19 and sealing plug 20. Scrubbing liquid reservoir 21 is formed by the addition of liquid through the fill/drain tube 19 from reversible pump 44.

Inside scrubbing chamber 18, an open-ended siphon tube 22 is externally attached through connection 23 to atomizing nozzle 16 whereby there is no fluid communication between siphon tube 22 and nozzle 16. Siphon tube 22 is attached essentially parallel to atomizing nozzle 16, with the siphon tube base 24 terminating just above the bottom of vessel 11. The siphon tube tip 25 is curved and terminates adjacent and directly above atomizing nozzle tip 26.

A coupling 27 joins vessel 11 to a funnel-shaped filter housing 30. The solvent-phobic membrane 28 is held within housing 30 by a conical support screen 29 which is brazed or otherwise conventionally secured to top plate 31. Top plate 31 sealingly seats onto housing 30 using an O-ring 33 and two screws 32. Scrubbed gas passing through the membrane 28 and support screen 29 exits concentrator 10 through outlet opening 34 in the top plate 31. Suction from source 42, e.g., a vacuum pump, is applied to outlet 34 via tubular conduit 44 as needed for controlled gas flow through vessel 10.

One embodiment of the invention capable of small sample testing utilizes a concentrator 10 weighing approximately 1 Kg with a length of approximately 20 cm. The atomizing nozzle 14 and glass vessel 11 are commercially available as a single unit from the Devilbiss Company of Somerset, Pa., under the name of Glass Nebulizer 40. Other material compositions used in this embodiment include: an (isothermal) ice-water bath 12, a glass inlet tube 17, a glass fill/drain tube 19, a rubber sealing plug 20, an aqueous solution scrubbing liquid reservoir 21, a glass siphon tube 22, a glass atomizing nozzle 26, a rubber coupling 27, a Teflon ® hydrophobic (solvent-phobic) membrane 28, a stainless steel wire cone support screen 29, a Teflon ® filter housing 30, a stainless steel top plate 31, and a rubber O-ring 33.

In operation of the described preferred embodiment, an aqueous extraction solution (scrubbing liquid), with a pH optimized for the trace gases to be extracted, was pumped through the fill/drain tube 19 to fill the bottom of the vessel 11 with a 3 ml reservoir 21. The fill/drain tube 19 was sealed, and air (contaminated with trace gases) from gas supply 40 was drawn through inlet tube 17, vessel inlet 13, and atomizing nozzle 16. Pressure for driving the air through nozzle 16 was supplied by the sample air itself; the air being delivered from pressurized tanks. In an alternative embodiment, the invention is suspended from an aircraft and the outside air is directly sampled without the need for additional pressurization, as the air velocity provides a pressure head sufficient to operate the invention. Additionally, the invention can be used at ground level by using a pump to draw air samples through the apparatus. The volumetric flow rate of the inlet air was regulated at approximately 8 l/min. As the jetted air left nozzle tip 26 and rushed by siphon tube tip 25, the scrubbing liquid from the reservoir 21 below was siphoned up through the siphon tube 22 and out into the jetted air. The scrubbing solution was aspirated at a rate of approximately 2.0 ml/min. The aspirated solution leaving siphon tube tip 25 was atomized by the air stream, thereby forming an air/droplet mist. The air/droplet mist was very fine, and as large liquid surface area was generated, thereby facilitating (mass) transfer of the trace gas contaminants from the air sample to the liquid. The mist moved upward through the scrubbing chamber 18 until it impinged upon the conical hydrophobic membrane 28. The hydrophobic membrane a was formed by shaping a Teflon ® filter (2 micrometer pore size Zeflour made by Membrana, Inc.) around a stainless steel wire cone support screen 29. The chosen filter material was necessarily chemically inert relative to the trace gases present in the air sample.

The membrane 28 offered little resistance to the exiting scrubbed gas flow. The liquid phase, however, was trapped inside the concentrator 10, as water droplets containing the removed trace gases collected on the membrane surface 28 and coalesced into larger droplets which subsequently rolled off the apex of conical membrane 28. These larger drops fell back into solution reservoir 21 and were recycled continuously through the aspiration-atomization-coalescence process. Make-up solution was added through fill/drain tube 19 as necessary to replace water lost as vapor through membrane 28. Such water loss was regularly minimized by immersing vessel 10 in an ice-water bath 12, this immersion having the effect of raising the solubility of the trace gases in the scrubbing solution. The cyclical concentration continued until the air supply was cut off, and the scrubbing solution was then drained from vessel 11 by reversible pump 46 via fill/drain tube 19. Any subsequent rinse solution was added to the originally drained solution, and the combined solution was subjected to quantitative analysis.

In one specific example of the exemplary method using the described embodiment, the extraction efficiency of the nebulization reflux concentrator was evaluated with trace mixtures of hydrogen chloride (HCl), ammonia ($NH_3$) and sulfur dioxide ($SO_2$) Hydrogen chloride mixtures in nitrogen were generated with a commercially available calibration system that utilizes the constant diffusion of HCl from a heated (80° C.) vial of an azeotropic $HCl/H_2O$ mixture. This system furnished about 175 ppmv of HCl in $N_2$. Ammonia was obtained from a pressurized aluminum cylinder containing 92±2 ppmv $NH_3$ in $N_2$. Sulfur dioxide was supplied from a pressurized aluminum cylinder containing 4.8±0.2 ppmv $SO_2$.

The effectiveness of the nebulization reflux technique for extraction of highly water soluble trace gases was evaluated with HCl and $NH_3$ Mixtures of HCl in $N_2$, and of $NH_3$ in $N_2$, were first passed through a two-stage fritted bubbler sampling train for quantification. The fritted bubblers were filled with 25 ml of aqueous extracting solution; $1 \times 10^{-5}$ M NaOH for HCl extractions, $4.5 \times 10^{-3}$ M HCl for $NH_3$ extractions. Almost total extraction of gaseous HCl and $NH_3$ was expected in these runs since the solution pH's were preadjusted for optimal trapping and since gas flow through the bubbles was kept low (50 cm$^3$/min). Results from these test runs are shown in Table I. It should be noted that the mixing ratios of HCl and $NH_3$ determined from these bubbler test runs are within six percent of the expected and/or assayed values.

TABLE I

Calculated Source Concentrations of NH₃ and HCl From Bubbler Extractions

| Run No. | NH₃ (1st Bubbler) | NH₃ (2nd Bubbler) | HCl (1st Bubbler) |
|---|---|---|---|
| 1 | 92.9 ppmv | NA | 168 ppmv |
| 2 | 91.4 | NA | 165 |
| 3 | 93.9 | NA | 167 |
| 4 | 97.3 | NA | 147 |
| 5 | 96.5 | NA | 162 |
| 6 | 93.9 | NA | 170 |
| 7 | 92.1 | 2.2 ppmv | 176 |
| 8 | 90.7 | 3.7 | 163 |
| 9 | 92.8* | 2.0 | 171 |
| 10 | 92.8* | 4.1 | 170 |
| 11 | 91.2* | 3.4 | NA |
| 12 | 90.8* | 3.0 | NA |
| mean, div | 92.9 + 2.1 | 3.1 + 0.8 | 165.9 + 7.8 |

*initial pH = 4.3

Results from the nebulization reflux concentrator 10 test runs appear in Table II. Although these runs were conducted utilizing identical 50 cm³/min flows of gaseous HCl or NH₃ mixture (as with the bubbler extractions), it was necessary to incorporate an additional 8 1/min flow of prepurified dry nitrogen into the gas stream to operate the atomizing nozzle 14. Extracting solution for these runs consisted of about 3 ml of either $1 \times 10^{-5}$ M NaOH for HCl, or $4.5 \times 10^{-3}$ M HCl for NH₃.

TABLE II

Calculated Source Concentrations of NH₃ and HCl From Nebulization Reflux Preconcentrator Extractions

| Run No. | NH₃ Analysis | HCl Analysis |
|---|---|---|
| 1 | 95.6 ppmv | 166 ppmv |
| 2 | 98.2 | 162 |
| 3 | 93.9 | 162 |
| 4 | 98.2 | 185 |
| 5 | 97.3 | 164 |
| 6 | 91.5 | 162 |
| 7 | 90.5 | 171 |
| 8 | 95.4 | 164 |
| 9 | 92.0 | 179 |
| 10 | 89.4 | 185 |
| 11 | 93.6 | 176 |
| 12 | NA | 188 |
| 13 | NA | 185 |
| 14 | NA | 179 |
| 15 | NA | 166 |
| mean, dev. | 94.4 + 3.1 | 172.9 + 9.9 |

Table II shows that the mixing ratios determined for HCl and NH₃ from these runs are in excellent agreement with assayed values and with the bubbler results shown in Table I. This result is even more significant when it is realized that the scrubber results were obtained at about 150 times the flow rate used with the bubbler, into about ⅛ the volume of extracting solution, and at about 1/150 of the gas phase analyte concentration.

A second series of experiments were conducted to evaluate the performance of the nebulization reflux concentrator in an extraction that involved both an initial gas absorption step and an induced chemical transformation. In these experiments, test runs were conducted in which gaseous SO₂ was either (1) passed through bubblers containing 0.1% H solution at 60 cm³/min, or (2) through the nebulization reflux concentrator driven with 8 1/min of ultra pure air also using a 0.1% H₂O₂ extracting solution. The H₂O₂ served to convert extracted SO₂ to sulfate. Data obtained during these series of runs are shown in Table III. The bubbler and scrubber results are in excellent agreement with the cylinder assay, and with each other. It is significant to note that the scrubber results were obtained at about 130 times the gaseous flow rates, in about ⅛ the volume of extracting solution, and at an effective SO₂ gas phase concentration of about 40 ppmv.

TABLE III

Calculated Source Concentrations of SO₂ From Bubbler and Nebulization Reflux (Scrubber) Extractions

| Run No. | SO₂ (1st Bubbler) | SO₂ (2nd Bubbler) | SO₂ (Scrubber) |
|---|---|---|---|
| 1 | 5.1 ppmv | NA | 4.7 ppmv |
| 2 | 4.6 | NA | 5.0 |
| 3 | 4.8 | NA | 4.6 |
| 4 | 4.6 | NA | 4.6 |
| 5 | 4.6 | 0.1 ppmv | 4.8 |
| 6 | 4.4 | 0.2 | 4.6 |
| 7 | 4.6 | 0.3 | 4.5 |
| 8 | 5.1 | 0.1 | 4.5 |
| mean, dev. | 4.7 + 0.3 | 0.2 + 0.1 | 4.7 + 0.2 |

In previous work, it was found useful to express the effectiveness of a bubbler extraction process in terms of the ratio of the maximum gas flow rate, $V_g$ (cm³/min), achievable without resulting loss of captured analyte to the minimum volume of extracting solution $V_x$ (ml). The maximum flow through the minimum volume translates into the most concentrated solution, ultimately facilitating chemical analysis. Though somewhat cursory, this approach allows relative comparisons to be made among extraction techniques and/or apparatus. For single bubbler extractions of HCl and NH₃, the bubblers used were found to perform without significant loss of capturing efficiency for $V_g/V_x$ ratios of about 300. At higher $V_g/V_x$ (>300), bubbler capturing efficiencies were observed to decline significantly. However, $V_g/V_x$ ratios of about 2700 were routinely used with the nebulization reflux concentrator without any detectable loss in captured analyte. Several runs were made at flow rates of 10 1/min ($V_g/V_x=3300$) with no apparent loss in scrubbing efficiency. The increased efficiency (up to 10 fold) of the nebulization reflux technique over bubbler/impinger extraction techniques translates into shorter sampling times, and thus, better temporal resolution for atmospheric trace gas measurements.

Although runs could have been made at flow rates greater than 10 1/min, considerable back pressure resulted from the nozzle restriction (0.5 atm. at 10 1/min); sampling flows of from 6–8 1/min were found most suitable for general scrubbing operations.

In describing the preferred embodiment of the invention, specific terminology has been resorted to for the sake of clarity and specific material compositions for the various parts have been described. However, the invention is not intended to be limited to the specific terms and materials so selected, and it is to be understood that each specific term and material described is intended to include all equivalents which could operate in a similar manner to accomplish a similar purpose.

Thus, although the invention has been described relative to a specific embodiment thereof, it is not so limited and numerous variations and modifications thereof will be readily apparent to those skilled in the art in the light of the above teaching. It is therefore to be understood that within the scope of the appended claims the invention may be practiced otherwise than as specifically described.

What is claimed as new and desired to be secured by Letters patent of the United States is:

1. Apparatus for removing trace constituents from a gas comprising, in combination:

a nebulizing vessel having an inlet and an exit, a reservoir of gas absorbing liquid solvent contained within said nebulizing vessel, an atomizing nozzle positioned inside said vessel in fluid communication with said vessel inlet and terminating above the level of said reservoir of gas absorbing liquid, a tubular gas inlet leading from a gas supply and disposed in sealed fluid communication with said vessel inlet and said atomizing nozzle, an open ended siphon tube attached parallel to said atomizing nozzle and having a first open end thereof disposed within said reservoir of liquid solvent and a second reduced diameter open tip end disposed adjacent the tip of said atomizing nozzle, a filter housing sealingly connected at one end thereof to said nebulizing vessel exit and in operative spaced relationship to said exit to preclude passage of gas except through said filter, a liquid solvent-phobic filter disposed within said filter housing, said filter being positioned so as to be in the path of any gas exiting from said vessel and serving to trap any liquid solvent coming in contact therewith while permitting gas flow to exit therethrough, an end closure for said filter housing and having an exit port therein permitting gas passing through said filter to exit from said apparatus, a top plate circumferentially sealed to and closing the end of said filter housing opposite to the end thereof connected to said nebulizing vessel, said top plate having an exit therethrough for removal of the gas filtered by said liquid solvent-phobic filter, a conical wire mesh screen disposed within said filter housing operatively spaced across said nebulizing vessel exit, said conical wire mesh screen serving as support structure for said liquid solvent-phobic filter with said filter mounted on the internal side of said screen forcing all egressing gas through said filter, whereby gas received from the gas supply travels through said tubular gas inlet to said atomizing nozzle and upon exit from said nozzle siphons liquid solvent from said reservoir to entrain the gas into a mist with the liquid soluble trace constituents in the gas flow going into solution, and the trace constituent free gas passing through said filter as the liquid droplets from the mist coalesce onto said filter and fall back into said reservoir.

2. Apparatus as in claim 1 wherein said conical wire mesh screen is secured to said top plate, and said top plate closes the end of said filter housing.

* * * * *